United States Patent [19]

Breslow

[11] 4,352,938
[45] Oct. 5, 1982

[54] EPOXY-AZIDOFORMATE COMPOUNDS

[75] Inventor: David S. Breslow, Wilmington, Del.

[73] Assignee: Hercules Incorporated, Wilmington, Del.

[21] Appl. No.: 86,601

[22] Filed: Oct. 19, 1979

Related U.S. Application Data

[60] Continuation of Ser. No. 702,637, Jul. 6, 1976, abandoned, and a continuation-in-part of Ser. No. 540,311, Jan. 10, 1975, abandoned, which is a continuation-in-part of Ser. No. 301,003, Oct. 26, 1972, abandoned, which is a division of Ser. No. 85,300, Oct. 29, 1970, abandoned, which is a division of Ser. No. 843,230, Jul. 18, 1969, Pat. No. 3,608,604.

[51] Int. Cl.³ .................... C07D 303/16; C07H 15/26
[52] U.S. Cl. ........................................ 549/553; 536/4; 536/53

[58] Field of Search .................... 260/348.46, 348.47; 536/53, 4

Primary Examiner—Norma S. Milestone
Attorney, Agent, or Firm—Marion C. Staves

[57] ABSTRACT

Disclosed are epoxy-azidoformate compounds of the formula

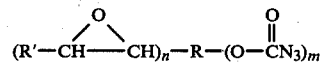

where R is a polyvalent organic radical, R' is a hydrogen, alkyl, cycloalkyl, aryl, aralkyl, and n and m are integers from 1 to 100. Also disclosed is the use of said epoxy-azidoformate compounds in modifying polymers, cross-linking polymers, and adhering polymers to certain substrates, e.g., glass and other polymers.

6 Claims, No Drawings

EPOXY-AZIDOFORMATE COMPOUNDS

This is a continuation of application Ser. No. 702,637, filed July 6, 1976, now abandoned, which is in turn a continuation-in-part of my copending application Ser. No. 540,311, filed Jan. 10, 1975, now abandoned, which is in turn a continuation-in-part of my application Ser. No. 301,003, filed Oct. 26, 1972, now abandoned, which is in turn a division of my application Ser. No. 85,300 filed Oct. 29, 1970, now abandoned, which is in turn a division of my application Ser. No. 843,230, filed July 18, 1969, now U.S. Pat. No. 3,608,604.

This invention relates to a new class of organic compounds and to their use. More particularly, this invention relates to a new class of epoxy-azidoformate compounds and their use in modifying polymers, cross-linking polymers and adhering polymers to certain substrates.

The compounds of this invention are represented by the generic formula

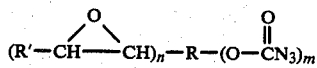

where R is a polyvalent organic radical, R' is a hydrogen, alkyl, cycloalkyl, aryl, or aralkyl radical, and n and m are integers, broadly each being 1 to 100, most preferably from 1 to 10. Generally, R will be an organic radical selected from the group consisting of radicals derived by the removal of two or more hydrogen atoms from alkanes such as, for example, methane, ethane, propane, butane, isobutane, pentane and its isomers, hexane and its isomers, heptane and its isomers, octane and its isomers, nonane and its isomers, decane and its isomers, dodecane and its isomers, octadecane and its isomers, and the like; cycloalkanes such as, for example, cyclopropane, cyclobutane, cyclopentane, cyclohexane, cycloheptane, cyclooctane, and the like; alkyl substituted cycloalkanes, such as, for example, propylcyclohexane, pentylcycloheptane, octylcyclohexane, ethylcyclohexane, methylcyclobutane, 1,2-, 1,3- and 1,4-dimethylcyclohexane, 1,2-, and 1,3-dimethylcyclopentane, and the like; arenes, such as, for example, benzene, naphthalene, biphenyl, and the like; alkyl substituted arenes, such as, for example, toluene, ethylbenzene, propylbenzene, butylbenzene, hexylbenzene, octylbenzene, 1,2,3-trimethylbenzene, o-, m- and p-xylene, o-, m- and p-diethylbenzene, and the like; alkylenediarenes, such as, for example, diphenyl methane, 1,2-diphenylethane, 1,4-diphenylbutane, 1,5-diphenylpentane, 1,1-diphenylpropane, 1,3-diphenylpropane, 2,2-diphenylpropane, 1,6-diphenylhexane, 1,8-diphenyloctane, and the like; alkyloxyalkanes, such as, for example, diethyl ether, dipropyl ether, dihexyl ether, didodecyl ether, dioctadecyl ether, 2,2,2-tris(methyleneoxymethylene)ethyl, 2,2-bis(allyloxymethylene)-2-methyleneoxymethylene ethyl, and the like; and the foregoing radicals with fluoro, chloro, bromo, or iodo substituents. In the above described R and R' radicals the said alkane and alkyl radicals will most preferably contain from 1 to 18 carbon atoms, the said cycloalkane and cycloalkyl radicals will most preferably contain from 3 to 8 carbon atoms and the said arene and aryl radicals will most preferably contain from 1 to 2 carbocyclic rings.

Specific compounds of this invention represented by the foregoing generic formula include but are not limited to:
2,3-epoxypropyl azidoformate
2,3-epoxybutyl azidoformate
2-chloro-4,5-epoxypentyl azidoformate
9,10-epoxyoctadecyl azidoformate
2,3-epoxyoctadecyl azidoformate
17,18-epoxyoctadecyl azidoformate
brominated 9,10-epoxyoctadecyl azidoformate containing an average of two bromines
chlorinated 9,10-epoxyoctadecyl azidoformate containing an average of two chlorines
fluorinated 9,10-epoxyoctadecyl azidoformate containing an average of two fluorines
iodinated 9,10-epoxyoctadecyl azidoformate containing an average of two iodines
tris-O-(2,3-epoxypropyl)pentaerythritol monoazidoformate having the formula

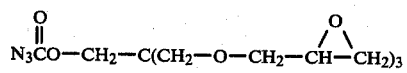

bis-O-(2,3-epoxypropyl)pentaerythritol bis-diazidoformate having the formula

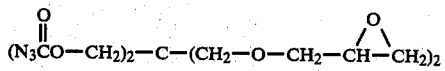

2,3-epoxypropyl-diallylpentaerythritol monoazidoformate having the formula

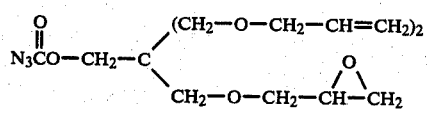

bis-O-(2,3-epoxypropyl)glycerine monoazidoformate having the formula

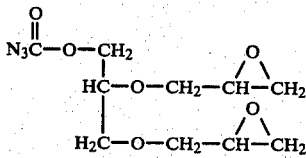

decaazidoformyloxy-O-(2,3-epoxypropyl) raffinose
azidoformyloxy-[deca-O-(2,3-epoxypropyl)] raffinose
3-(epoxyethyl)cyclopentyl azidoformate
3-(epoxyethyl)cyclobutyl azidoformate
2-epoxyethyl)cyclopropyl azidoformate
4-(epoxyethyl)cycloheptyl azidoformate
4-(epoxyethyl)cyclooctyl azidoformate
2,3-dimethyl-4-(epoxyethyl)cyclohexyl azidoformate
4-(2,3-epoxypropyl)cyclohexyl azidoformate
2,4-bis(epoxyethyl)cyclohexyl azidoformate
4-(epoxyethyl)phenyl azidoformate
2,3,5-trichloro-4-(epoxyethyl)phenyl azidoformate
4-(epoxyethyl)phenylethyl azidoformate
3-(epoxyethyl)benzyl azidoformate
3-cyclohexyl-2,3-epoxypropyl azidoformate
4-phenyl-2,3-epoxybutyl azidoformate
4-(2,3-epoxypropyl)phenyl azidoformate
3-(2,3)epoxypropyl)phenyl azidoformate 2-(2,3-epoxypropyl)phenyl azidoformate
4-(epoxyethyl)naphthyl azidoformate
4'-(epoxyethyl)biphenyl-1-azidoformate
2,3-dimethyl-4-(epoxyethyl)phenyl azidoformate
4'-(epoxyethyl)diphenylmethane-1-azidoformate
3-cyclopropyl-2,3-epoxybutyl azidoformate
3-cyclooctyl-2,3-epoxybutyl azidoformate
3(diphenyl-2yl)-2,3-epoxypropyl azidoformate
3(diphenyl-3yl)-2,3-epoxypropyl azidoformate
3(diphenyl-4yl)-2,3-epoxypropyl azidoformate
3-phenyl-2,3-epoxypropyl azidoformate
2,5-dichloro-4-(epoxyethyl)cyclohexyl azidoformate
2-iodo-4-epoxyethyl)cyclohexyl azidoformate
2,3,5,6-tetrafluoro-4-(epoxyethyl)phenyl azidoformate
3-bromo-4-(epoxyethyl)phenyl azidoformate
4-(epoxyethyl)cyclohexyl azidoformate
9,10-epoxydecyl azidoformate
9,10-epoxydecyl-2,5-bis-diazidoformate
2,3-epoxypropyloxypropyl azidoformate
2,3-epoxypropyloxyethyl azidoformate The epoxy azidoformates of this invention range from liquids to solids at room temperature and atmospheric pressure and are soluble in chlorinated hydrocarbons, aromatics, acetone, etc. They have a characteristic infrared spectrum with a strong azide peak around 2135 cm$^{-1}$. When heat is applied to the compounds of this invention they decompose giving off nitrogen; as the temperature increases the overall decomposition rate increases. The azidoformate radicals of the compounds readily react with receptive polymers and combine therewith when heated. They also combine with ethylenically unsaturated hydrocarbon groups in a variety of compounds. In so doing, the epoxy portion of the compound remains free and unreacted. While the epoxy portion is heat stable it readily reacts when contacted with amines or carboxylic acids.

The epoxy-azidoformate compounds of this invention can be prepared by various methods. Most preferably these compounds will be prepared by the epoxidation of an unsaturated azidoformate compound with peracetic acid or perbenzoic acid. The reaction is usually carried out at a temperature below 100° C. in a solvent. Acetic acid is the most preferred solvent when using peracetic acid but other solvents can be used such as methylene chloride, acetone, ethyl acetate, chloroform, benzene, and the like.

As indicated above, this invention includes the use of the unique epoxy-azidoformate compounds in modifying polymers, cross-linking polymers and adhering polymers to certain substrates. All of these uses involve the reaction of the azidoformate portion or portions of the epoxy-azidoformate compounds with a receptive polymer. In this specification receptive polymer means a polymer having in each polymer chain at least one and generally more than one monomer unit capable of combination reaction with an azidoformate radical of a compound of this invention, whereby the residue of the compound is chemically bonded to the polymer. Nearly all polymers are receptive polymers. Preferred examples of a receptive polymer include all types of hydrocarbon polymers including saturated and unsaturated, linear and nonlinear, crystalline and amorphous, homopolymers, copolymers, terpolymers, and the like; for example, polyethylene, polypropylene, polystyrene, styrene-butadiene rubber, butyl rubber, natural rubber, polybutadiene, polyisobutylene, ethylene-propylene copolymer, cis-1,4-polyisoprene, ethylene-propylene-dicyclopentadiene terpolymer, and the like; and blends of these polymers with each other and blends of these polymers with organic nonhydrocarbon polymers. In addition to hydrocarbon polymers preferred examples of a receptive polymer include a large number of organic nonhydrocarbon polymers including homopolymers, copolymers, terpolymers and the like. Typical of these organic nonhydrocarbon polymers are cellulose esters, such as, for example, cellulose acetate-butyrate, cellulose acetate-propionate, cellulose acetate, cellulose propionate, cellulose butyrate, and the like; cellulose ethers, such as, for example, hydroxyethyl cellulose, hydroxypropyl cellulose, and the like; polyesters such as poly(ethylene glycol terephthalate) drying and nondrying alkyd resins and the like; poly(alkylene oxide) polymers, such as poly(ethylene oxide), poly(propylene oxide), poly(ethylene oxide-propylene oxide); polyamides such as nylon, and the like; allyl pentaerythritol derivatives such as, for example, the condensate of triallyl pentaerythritol with diallylidene pentaerythritol, esters of triallyl pentaerythritol and drying oil fatty acids, and the like; poly(vinyl alkyl ethers) such as, for example, poly(vinyl methyl ether) and the like; poly(vinyl acetals) such as, for example, poly(vinyl butyral) and the like; vinyl chloride polymers having a vinyl chloride content of at least 10 mole percent, such as, for example, poly(vinyl chloride), vinyl chloride-vinyl acetate copolymers, vinyl chloride-vinylidene chloride copolymers, vinyl chloride-fumaric acid copolymers, vinyl chloride-vinyl acetal copolymers, such as, for example, the vinyl chloride-vinyl butyral copolymers, vinyl chloride-vinylidene chloride-acrylonitrile terpolymers, and the like; nitrocellulose; chlorinated natural rubber; sulfochlorinated polyethylene; polysulfide rubber; polyurethane rubber; poly(vinyl acetate); ethylene-vinyl acetate copolymers; poly(vinylidene chloride); vinylidene chloride-acrylonitrile copolymers; ethyl acrylate-2-chloroethyl vinyl ether copolymers; poly(ethyl acrylate); poly(ethyl methacrylate); poly[3,3-bis(chloromethyl)oxetane]; vinyl modified poly(dimethylsiloxane); polychloroprene; butadiene-acrylonitrile copolymers; and the like.

The modified polymers of this invention resulting from the reaction of the azidoformate portion or portions of the epoxyazidoformate compounds with the above receptive polymers are both useful in themselves and necessary intermediates in further modifications of this invention. The amount of epoxy-azidoformate compound used to modify a receptive polymer will depend upon the desired end use. In general, however, the amount will be from about 0.01% to about 40% by weight based on the weight of the polymer. The resulting modified polymers are quite stable and generally have physical properties similar to the unmodified polymers. However, the thus modified polymers exhibit new and improved static properties, adhesion properties, launderability, etc. Modification can be carried out by admixing the required amount of epoxy-azidoformate compound with a receptive polymer and heating to a temperature sufficient to react the azidoformate portion or portions of the compound with the polymer. The temperature will be in the range of from about 80° C. to about 200° C.

In one modification of this invention the epoxy-azidoformate compounds are used to bond various polymers to a substrate selected from siliceous materials, metals and other polymers. A typical example of the bonding process of this invention is the bonding of an α-olefin polymer such as polypropylene to a glass substrate. The said glass substrate, such as glass fibers, glass cloth, plate glass, etc., would first be treated with an amino silane compound. In so doing, the silane portion of the compound would react with the substrate, leaving the amine portion free for later reaction with an epoxy portion of an epoxy-azidoformate compound. Next, polypropylene, having been modified with an epoxy-azidoformate compound so as to react the azidoformate portion with the polymer leaving the epoxy portion free, is placed in contact with the above-described treated glass. The free amine groups on the treated glass react with a free epoxy group on the modified polymer forming a tight bond between the polymer and the glass substrate.

Another typical example of bonding a polymer to a substrate using an epoxy-azidoformate compound is the bonding of poly(ethylene terephthalate) tire cord to rubber tire stock. The polyester tire cord is first modified with the epoxy-azidoformate compound. In so doing the azidoformate portion or portions react with the polyester leaving the epoxy portion or portions free. Next, the tire cord is generally coated with a conventional tire cord adhesive comprising a mixture of a phenol-aldehyde resin and a rubber terpolymer latex prepared from a vinyl aryl monomer, a diene monomer, and a vinyl pyridine monomer, and then cured. If desired, the coating of conventional tire cord adhesive can be omitted with a proportionate decrease in adhesive strength. Finally the thus treated tire cord is embedded in a vulcanizable rubber tire stock and cured. While polyester tire cords are mentioned, it will be understood that various other synthetic fibers can be incorporated in rubber tire stock in accordance with this invention. Such other tire cord fibers are for example, polyolefin, polyamide, polycarbonate, rayon, etc., and mixtures of these fibers. Improved adhesion of the synthetic fibers to the rubber tire stock can be obtained by the process of this invention no matter what the physical form of the fibers e.g. monofilament, multifilament, twisted, braided, etc. The tire cord can be treated with the epoxy-azidoformate compound by any conventional means, for example, by dipping, spraying, brushing, or running the cord over a coated roll with a solution of the epoxy-azidoformate compound in a suitable liquid. The epoxy-azidoformate compound can also be applied as an aqueous suspension, emulsion, or dispersion. After the epoxy-azidoformate compound is applied, the cord is heated to a temperature at which the azidoformate portion or portions react with the synthetic fiber. Various amounts of the epoxy-azidoformate compound can be used. The optimum amount will depend upon the amount of modification desired, the specific epoxy-azidoformate compound used, etc. In general, the amount added, based on the cord, will be from about 0.1% to about 10% by weight. As indicated above, the thus modified cord is generally coated with a conventional tire cord adhesive. This adhesive comprises a mixture of (1) a resin, preferably prepared from resorcinol and formaldehyde with (2) a terpolymer latex, which is preferably a styrene-butadiene-vinyl pyridine terpolymer. The vinyl pyridine content of the terpolymer is usually about 5% to about 25%, the styrene content about 5% to about 35%, and the butadiene content from about 50% to about 85%. The latex is applied to the modified tire cord by dipping, spraying, brushing, running the modified cord over a coated roll or other conventional procedure. The amount of latex added will be from about 2% to about 10% based on the weight of the cord. The thus coated cord will be cured at a temperature of from about 190° C. to about 235° C. for a period of time of from about 0.5 to about 2 minutes. The thus treated cord is then embedded in a conventional rubber tire stock and cured under pressure. The vulcanizable tire stocks in which the treated cord can be embedded as a reinforcing medium include natural rubber, and synthetic rubbers such as styrene-butadiene rubbers, ethylene-propylene-diene terpolymer rubbers, polybutadiene, polyisoprene and mixtures and blends thereof with suitable fillers, pigments, antioxidants, and cross-linking (i.e. vulcanizing) agents such as sulfur, peroxides, etc.

Another typical example of bonding a polymer to a substrate using an epoxy-azidoformate compound is the bonding of an α-olefin polymer such as polyethylene to a metal substrate. The metal substrate will first be treated with a priming agent. The priming agent is a polyfunctional compound, such as an amino silane compound, which possesses a portion or portions which bond to the metal and another portion or portions which remain free to react with the epoxy group or groups on the epoxy-azidoformate compounds. The process of bonding polyethylene to a metal substrate can be carried out in various ways. For example, the substrate can be coated with a solution or suspension of the priming agent, allowed to dry, then coated with a solution or suspension of the epoxy-azidoformate compound, allowed to dry and finally contacted with the polyethylene at the decomposition temperature of the azide. By another method, the substrate can be coated with a solution or suspension of the priming agent, allowed to dry, then contacted with a solution or mixture of both the epoxy-azidoformate compound and the polyethylene and finally heated to the decomposition temperature of the azide. By still another method the priming agent, epoxy-azidoformate compound and polyethylene can be deposited together on the substrate and then heated.

The substrates to which the polymers may be bonded in accordance with this invention include siliceous materials such as glass, asbestos, sand, clay, concrete, stone, brick, ceramic materials, etc.; metals such as aluminum, cadmium, chromium, copper, magnesium, nickel, silver, tin, iron, titanium, zinc, etc., alloys of the metals such as steel, brass, bronze, nickel chrome, etc. and including metals which have been surface treated with phosphates, chromates, etc. or on the surface of which oxides have formed; and other polymers. By the term "other polymers" is meant any polymer other than the polymer to which it is to be bonded. These substrates to which the polymers may be bonded can be in various forms such as sheets, plates, blocks, wires, cloth, fibers, particles, etc.

In another modification of this invention the epoxy-azidoformate compounds are used to cross-link receptive polymers. The polymer to be cross-linked is admixed with from about 0.1% to about 20% by weight of an epoxy-azidoformate compound and heated to a temperature sufficient to react the azidoformate portion or portions of the compound with the polymer. To affect cross-linking the thus modified polymer is treated with a polyfunctional compound which will react with the free epoxy groups on the polymer. Various polyfunctional compounds can be used to affect the cross-linking, however, most preferred are the polycarboxylic acids and anhydrides such as oxalic acid, phthalic acid, phthalic anhydride, pyromellitic anhydride, etc. and the polyamines, such as m-phenylenediamine; diethylenetriamine, 4,4'-methylenedianiline, etc. When using one of these compounds, the carboxylic acid groups or amino groups react with the free epoxy groups tying together, i.e. cross-linking, the polymer chains.

The following examples will serve to illustrate the invention, all parts and percentages being by weight unless otherwise indicated.

EXAMPLE 1

This example illustrates the preparation of 2,3-epoxybutyl azidoformate.

To a slurry comprising 110 parts of sodium azide, 200 parts of water, 158 parts of acetone and 670 parts methylene chloride was added 115 parts of crotyl chloroformate with rapid stirring at room temperature. After stirring for 24 hours the orange-colored reaction mixture was diluted with 200 parts of water, separated, the organic layer washed with water, and dried over sodium sulfate. Removal of the solvent at room temperature yielded 112 parts of a clear colorless oil comprising crotyl azidoformate. A solution of 50 parts of the crotyl azidoformate in 420 parts of glacial acetic acid and 3 parts of anhydrous sodium acetate was cooled to 20° C. To the crotyl azidoformate solution was added, with agitation, 40% peracetic acid in an amount in excess of that required to convert the crotyl groups to epoxybutyl groups. The reaction was allowed to slowly come to room temperature and stirred until the theoretical amount of peracetic acid had been consumed. The reaction mixture was tested periodically to determine the amount of peracetic acid present. At the end of the fourth day the reaction was diluted with 600 parts of water and then extracted twice with 400 parts of methylene chloride. The methylene chloride solution was in turn washed with water and then dried over sodium sulfate. After removing the solvent 47 parts of 2,3-epoxybutyl azidoformate was obtained. The product was a light colored oil. Analysis for azide by nitrogen evolution showed that the compound contained approximately 98.7% of the theoretical amount. An analysis for oxirane oxygen showed that the compound contained approximately 91% of the theoretical amount. A typical infrared spectrum of this product displayed a strong azide peak at 2135 cm$^{-1}$.

EXAMPLE 2

This example illustrates the preparation of 9,10-epoxyoctadecyl azidoformate.

Oleyl azidoformate was prepared from oleyl chloroformate using sodium azide as described in Example 1. A solution of 84.5 parts of the oleyl azidoformate in 420 parts of glacial acetic acid containing 2 parts of sodium acetate was cooled to 20° C. To this solution was added with agitation, 40% peracetic acid in an amount in excess of that required to convert the oleyl groups to epoxyoctadecyl groups. The reaction was followed by testing for the presence of peracetic acid. After seven hours the reaction had ceased as indicated by the disappearance of peracetic acid. After 24 hours the reaction was diluted with 800 parts of methylene chloride and 600 parts of water. The methylene chloride layer was washed with water 6 times and then dried over sodium sulfate. Removal of the methylene chloride solvent left 82 parts of a colorless oil consisting essentially of 9,10-epoxyoctadecyl azidoformate. Analysis for the presence of azide by nitrogen evolution showed that the compound contained approximately 96% of the theoretical amount.

EXAMPLE 3

This example illustrates the preparation of a mixed epoxidation product of the azidoformate of the triallyl ether of pentaerythritol.

To a solution of 43 parts of the azidoformate of the triallyl ether of pentaerythritol in 315 parts of glacial acetic acid containing 1 part of sodium acetate at room temperature was added with agitation 40% peracetic acid in an amount in excess of that required to convert one of the allyl groups to an epoxy group. After stirring for 48 hours the reaction was diluted with 750 parts of water and 535 parts of methylene chloride. The methylene chloride layer was removed and washed with water 5 times and then dried over sodium sulfate. Removal of the methylene chloride solvent left 39 parts of a clear colorless oil consisting essentially of the epoxidation product of the azidoformate of the triallyl ether of pentaerythritol. Analysis of the product showed that it contained 13.6% azido nitrogen and 4.2% oxirane oxygen. The oxirane oxygen analysis indicates that the product is a mixture of the mono- and di-epoxidation product.

EXAMPLE 4

This example illustrates the preparation of another mixed epoxidation product of the azidoformate of the triallyl ether of pentaerythritol.

To a solution of 100 parts of m-chloroperoxybenzoic acid in 1125 parts of chloroform 50.8 parts of the azidoformate of the triallyl ether of pentaerythritol were added keeping the temperature between 25°–34° C. Sufficient m-chloroperoxybenzoic acid was present to convert all of the unsaturation to epoxy groups. Stirring was continued at room temperature for three days until the peroxide content of the reaction mixture no longer decreased.

The solid reaction by-products which formed were filtered off and discarded. The chloroform solution was washed repeatedly with 10% aqueous sodium bisulfite and 10% aqueous sodium bicarbonate and finally twice with 300 parts of water. After drying over magnesium sulfate the solvent was removed by evaporation under reduced pressure below 60° C. The product consisted of 56.7 parts of a thick pale yellow liquid. Analysis of the product showed that it contained 11.1% azido nitrogen (99.1% of theoretical) and 9.67% oxirane oxygen (75.2% of theoretical). The oxirane oxygen analysis indicates that the product is a mixture of the di- and tri-epoxidation product.

EXAMPLE 5

This example illustrates the use of the epoxy-azidoformate compound of Example 1 in bonding polypropylene to glass cloth.

Twelve ply laminates of glass cloth and polypropylene film were prepared using 181 style electrical glass woven cloth, heat cleaned and having a weight of 8.9 ounces per sq. yd., and 5 mil film of crystalline polypropylene having a melt index ($I_2$ at 230° C.) of 4.0. Sheets of the glass cloth were immersed in a benzene solution of α-aminopropyltriethoxysilane and 2,3-epoxybutyl azidoformate. The two ingredients were present in the solution in approximately a 1:1 mole ratio. The thus treated cloth was allowed to dry overnight and then laid up to form the laminate by alternating plies of the treated glass cloth and sheets of the polypropylene film. The resulting assembly was compression molded at a temperature of 220° C. for 5 minutes at contact pressure, 3 minutes at 220° C. under a pressure of 500 p.s.i. and then cooled to 23° C. under 500 p.s.i. pressure to form a ⅛ inch thick laminate. A control laminate was prepared exactly as described above except for the omission of the epoxy-azidoformate compound. Test specimens 1 in. ×3 in. were cut from the laminates and tested for flexural strength according to ASTM D-790 on a two-inch span at 0.05 in. per min. cross-head speed. The results are tabulated below:

|  | Flexural Strength (psi) |
| --- | --- |
| Treated sample | 28,000 |
| Control | 18,000 |

EXAMPLE 6

This example illustrates the use of the epoxy-azidoformate compound of Example 3 to improve the adhesion of polyester tire cord to rubber tire stock.

Poly(ethylene terephthalate) tire cord 1,000 denier and 3 ply under about 500 grams of tension was passed twice through a trough containing a 5% solution of the epoxy-azidoformate compound in trichloroethylene. The cord was next passed through two ovens in series at 200° F. and 400° F. Residence times in the ovens were 65 and 54 seconds respectively. The cord dip pick-up was approximately 1% by weight. The modified cord was next coated with a conventional latex adhesive, prepared as follows: To a solution of 0.24 part of sodium hydroxide in 192.8 parts of water was added 8.8 parts of resorcinol with continued stirring until a complete solution was achieved. Then 12.2 parts of 37% formaldehyde was added. The solution was aged for approximately 5 hours at about 75° C. and then added slowly to a mixture of 48 parts water and 19 parts of a latex comprising a terpolymer of styrene, butadiene and vinyl pyridine, the monomers being present in a ratio of approximately 50:70:15. The mixture was stirred slowly for 15 minutes and its pH adjusted to 10.3 using concentrated ammonium hydroxide. The resulting gray-violet latex contained approximately 20% solids. The epoxy-azidoformate modified cord was passed twice through a trough of the latex under a tension of 500 grams and then dried and cured for 54 seconds at a temperature of 430° F.

The thus coated cord was then vulcanized with a rubber tire stock in the form of ⅜ inch H-specimens. The rubber tire stock has the following formulation:

| Compounds | Parts |
| --- | --- |
| Natural rubber (smoked sheet) | 80 |
| Styrene butadiene rubber | 20 |
| Semi-reinforcing furnace black | 25 |
| Zinc Oxide | 5 |
| Stearic Acid | 2 |
| Polytrimethyldihydroquinoline | 1 |
| Heavy pine tar | 0.5 |
| Benzothiazyl disulfide | 1 |
| Tetramethyl thiuram disulfide | 0.1 |

| Compounds | Parts |
| --- | --- |
| Sulfur | 2.6 |

The test specimens were cured for 45 minutes at a temperature of 307° F. After several hours conditioning at room temperature the H-specimens were pulled apart on a tester according to the procedure of ASTM D-2138-62T. An average (6 test specimens) of 35.7 pounds was required to overcome the tire cord-rubber adhesion. A control specimen treated exactly the same as above except for the epoxy azidoformate modification of the tire cord gave an average of 12.6 pounds required to overcome the tire cord-rubber adhesion.

What I claim and desire to protect by Letters Patent is:

1. An epoxy-azidoformate compound having the general formula

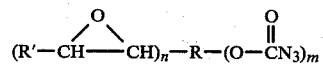

where R is a polyvalent organic radical, R' is a radical selected from the group consisting of hydrogen, alkyl, cycloalkyl, aryl and aralkyl radicals, and n and m are integers from 1 to 100.

2. An epoxy-azidoformate compound having the general formula

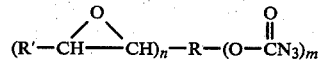

where R is an organic radical selected from the group consisting of radicals derived by the removal of two or more hydrogen atoms from alkanes, cycloalkanes, alkylcycloalkanes, arenes, alkyl substituted arenes, alkylenediarenes, dialkylcycloalkanes, alkyloxyalkanes, and the foregoing radicals with fluoro, chloro, bromo or iodo substituents, R' is a radical selected from the group consisting of hydrogen, alkyl, cycloalkyl, aryl, and aralkyl radicals and n and m are integers from 1 to 10.

3. An epoxy-azidoformate compound having the general formula

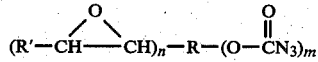

where R is an organic radical selected from the group consisting of radicals derived by the removal of two or more hydrogen atoms from alkanes, cycloalkanes, alkyl substituted cycloalkanes, arenes, alkyl substituted arenes, alkylenediarenes, alkyloxyalkanes, and the foregoing radicals with fluoro, chloro, bromo or iodo substituents, R' is a radical selected from the group consisting of hydrogen, alkyl, cycloalkyl, aryl, and aralkyl radicals, and n and m are integers from 1 to 10, said alkane and alkyl radicals containing from 2 to 18 carbon atoms, said cycloalkane and cycloalkyl radicals containing 3 to 8 carbon atoms and said arene and aryl radicals containing 1 to 2 carbocyclic rings.

4. 2,3-Epoxybutyl azidoformate.

5. 9,10-Epoxyoctadecyl azidoformate.

6. A mixed epoxidation product of the azidoformate of the triallyl ether of pentaerythritol.

* * * * *

UNITED STATES PATENT AND TRADEMARK OFFICE
CERTIFICATE OF CORRECTION

PATENT NO. : 4,352,938
DATED : October 5, 1982
INVENTOR(S) : David S. Breslow

It is certified that error appears in the above-identified patent and that said Letters Patent are hereby corrected as shown below:

Column 9, line 43 " 19 " should read -- 195 --.

Signed and Sealed this

Twenty-eighth Day of December 1982

[SEAL]

Attest:

GERALD J. MOSSINGHOFF

Attesting Officer

Commissioner of Patents and Trademarks